United States Patent [19]

Selker

[11] Patent Number: 4,974,614

[45] Date of Patent: Dec. 4, 1990

[54] DENTAL FLOSS

[76] Inventor: Frank Selker, 424 Dell Ave., Mt. View, Calif. 94043

[21] Appl. No.: 233,222

[22] Filed: Aug. 18, 1988

[51] Int. Cl.[5] ............................................. A61C 15/00
[52] U.S. Cl. ................................................... 132/321
[58] Field of Search ............... 132/321, 322, 323, 324, 132/325, 326, 327, 328, 329; 433/136

[56] References Cited

U.S. PATENT DOCUMENTS

| | | | |
|---|---|---|---|
| 1,149,376 | 8/1915 | Leonard et al. | 132/323 |
| 1,815,408 | 7/1931 | Jordan | 132/323 |
| 1,997,467 | 4/1935 | Manley | 433/136 |
| 2,702,555 | 2/1955 | De Mar | 132/323 |
| 2,811,162 | 10/1957 | Brody | 132/323 |
| 3,837,351 | 9/1974 | Thornton | 132/321 |
| 3,896,824 | 7/1975 | Thornton | 132/321 |
| 3,930,059 | 12/1975 | Wells | 132/321 |
| 4,008,727 | 2/1977 | Thornton | 132/321 |
| 4,016,892 | 4/1977 | Chodorow | 132/323 |
| 4,142,538 | 3/1979 | Thornton | 132/321 |
| 4,277,297 | 7/1981 | Thornton | 156/161 |
| 4,550,741 | 11/1985 | Krag | 132/321 |
| 4,633,892 | 1/1987 | Charatan | 132/321 |

*Primary Examiner*—John J. Wilson

[57] ABSTRACT

Improved dental floss comprising a first end, a central portion and a second end, with the first and second ends having relatively increased cross-sectional dimensions relative to the central portion. The increased cross-sectional dimensions of the end portions enhance the ease and comfort of holding the floss during use. The floss may be dispensed from a continuous roll, with a means of cutting the floss so that each length has relatively thickened ends. The floss may also be dispensed in convenient pre-cut lengths, each having thickened end portions and a relatively narrow central portion.

5 Claims, 2 Drawing Sheets

DENTAL FLOSS

BACKGROUND

It is well known that a length of string is useful for cleaning portions of teeth not readily accessible to brushing. This string is commonly referred to as dental floss (or just floss) and the use of floss is referred to as flossing. Dental floss is commonly a loosely twisted polymer-based string, which may be flattened into a band. It is fairly fine in gauge, with the cross-sectional dimensions of a band being on the order of 0.01 inches in thickness by 0.03 inches in width. It is sometimes impregnated or coated with a resin or wax.

A common way of using floss is to cut a piece one to two feet in length, hold one end in each hand, and use the fingers to guide the floss between and around the teeth. The ends are often wrapped snugly around one or more fingers in order to obtain a firm grasp of the ends. While this is simple and provides good control of the floss, it can aslo be difficult to hold the ends of the floss so that it does not slip from the hand during use. Furthermore, the fine gauge floss, which permits access to the spaces between teeth, tends to cut into the fingers and hand when it is held under tension. These problems are exacerated because the user's hands are often wet during flossing, which makes the user's hands slippery and the user's skin less tough than when dry.

SUMMARY

In accordance with the current invention dental floss is provided which has a narrow central portion which is suitable for cleaning the teeth and gums, but has thicker or wider portions at each end which are easier and more comfortable to hold.

OBJECTS AND ADVANTAGES

Many people find conventional dental floss difficult to hold firmly enough so that is does not slip in the hands during use. It is an object of the present invention to provide an improved floss which is easier to hold than conventional dental floss.

Many people find conventional dental floss uncomfortable or painful to hold because the thin floss tends to cut into fingers and hands, particularly when the hands are wet. It is an object of the present invention to provide a floss that is more comfortable to hold and use.

A further advantage of the present invention is that the improved dental floss will be easier to use by individuals who have impaired hand strength or coordination due to disabilities. An example of such a disability is arthritis which occurs among older people.

A further advantage of the present invention is that the floss may be readily dispensed in pre-cut pieces which can be more convenient to use than conventional floss. This convenience may contribute to increased usage.

There is a high value to increasing the use of dental floss, since costly and unpleasant tooth decay and gum disease would be reduced. Flossing is an important prophylactic measure to preventing tooth decay and gum disease. By reducing the discomfort and difficulty associated with the use of dental floss, the benefits of flossing may be more widely realized.

Further objects and advantages of the invention will become apparent and manifest in relation to the description below and the attached figures illustrating, in a non-limiting manner, embodiments of the invention.

BRIEF DESCRIPTIONS OF FIGURES

DETAILED DESCRIPTION OF THE INVENTION

Figure 1:
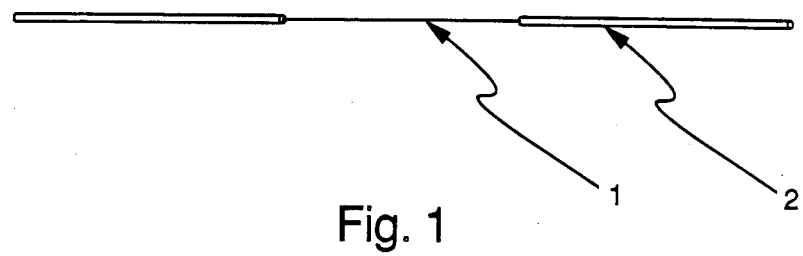
FIG. 1 shows a length of improved dental floss.
Figure 2:
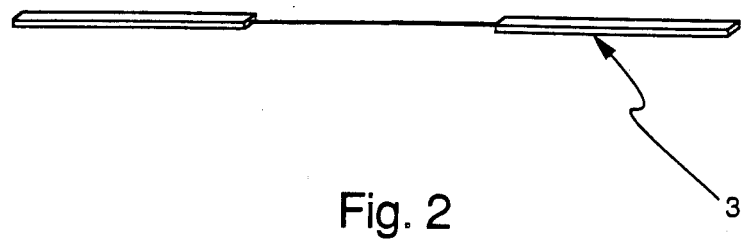
FIG. 2 shows a length of improved dental floss which is partially flattened into a band.

The object of this invention is an improved dental floss which has a center portion that is of a fine gauge, like commonly available dental floss, together with end portions that are thickened to provide for easier and more comfortable grasping by the user. The improved floss is used in lengths of about 10 to 24 inches. About one third of the total length, in the center portion, is of a fine gauge and about two-thirds of the length, one-third at each end, is thickened. FIG. 1 shows a single length of the improved dental floss with a narrow portion 1 and thick portions 2. FIG. 2 shows a preferred embodiment in which the floss is flattened into a band.

The fine gauge or narrow central portion (heretofor referred to as the "narrow portion") of the improved floss is similar to commonly available floss. The narrow portion may be made of natural fibers or of polymer fibers, such as nylon (polyamide) or polyolefin, formed into a string. The cross-sectional dimensions of the narrow portion will be sufficiently small so that it may move between adjacent teeth, or between a tooth and the adjacent gum. The cross-sectional area of the narrow portion will be on the order of 0.0001 to 0.001 square inches. The narrow portion of the floss may be flattened into a band. It may also be impregnated or coated with a polymer resin or wax, flavored, or colored much like commonly available floss.

The relatively thick end portions 2 (heretofore referred to as the "thick portions") have a cross-sectional area that is at least 20% greater than the cross-sectional area of the narrow portion. The thick portions may also be bands which are wider than the narrow portion. The thick portions can be thickened relative to the narrow portions in a number of ways. In one embodiment the floss is manufactured from a loose, relatively thick and soft yarn. Portions or all of the yarn are treated with a resin or wax. The portions to be made narrow are then drawn taught, so that the fibers roughly align, giving a relatively narrow cross-section. These narrow portions are then pressed, treated or cured so that the resin or wax fixes the fibers in the portion with a narrow cross-section in the relatively narrow configuration. This may also be achieved without a resin or wax treatment if the fibers are drawn tight at a temperature approaching the thermoplastic temperature for the fiber material. The thick portions can also be treated with a resin or wax which, when cured, provides body to the larger diameter portions. The result is floss having portions with relatively larger cross-sectional dimensions alternating with portions with relatively smaller cross-sectional dimensions.

In another embodiment the thick portions are enlarged relative to the narrow portion through the use of resin or elastomere coating. The coating can be sprayed onto floss, painted or rolled onto floss, or the floss can be dipped into a bath of the coating material. The method of application is chosen to be consistent with material properties of the coating, and to permit coating portions while leaving the relatively narrower portions uncoated. This coating provides a moderately soft (e.g., 65 to 90 on the D Durometer scale), rubber-like surface which is comfortable to grasp. The surface is textured or impregnated with abrasive particles to contribute to the ease of holding the floss without slipping. The floss is flattened into a band, so that when wrapped around the fingers the thick portion provides an increased surface over which force is distributed. The means for achieving relatively thick portions adjacent to relatively narrower portions are not limited to those in the described embodiments.

Figure 3:
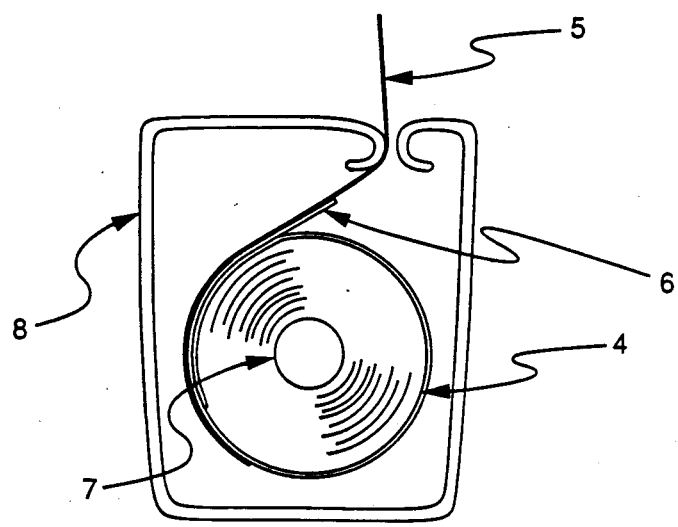
FIG. 3 shows a system for dispensing pre-cut lengths of improved dental floss from a roll.

In the preferred embodiment the improved floss is dispensed in pre-cut lengths. This is convenient for the user, and assures that the user obtains pieces of floss with the narrow portion centered between the two thick end portions. FIG. 3 shows pre-cut lengths dispensed from a roll 4. The pre-cut portions are overlapped on the roll 4. Successive lengths are ligthly bonded so that as one length 5 is drawn from the dispenser container 8 the roll 4 turns on axle element 7 and the beginning of the next length 6 is drawn out of the container. This is analogous to the way facial tissues are packaged: as each one is drawn out, the next is left partially out of the box and ready to grasp. Methods of lightly bonding, successive lengths include pressing them together to acheive adhesion, inter-twinning successive strands (e.g., twisting successive strands together), or using an adhesive that detachably bonds successive pieces of floss.

Figure 4:
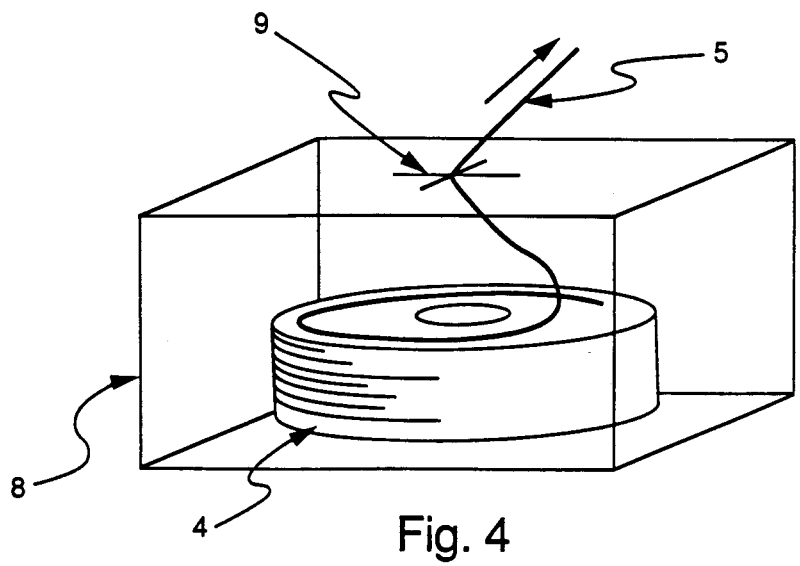
FIG. 4 shows another system for dispensing pre-cut lengths of improved dental floss.

FIG. 4 shows another dispenser system for pre-cut lengths of the improved floss. This dispenser is similar to that shown in FIG. 3 except that the bulk of the packaged floss 4 does not turn. The floss in the package 8 is largely stationary with lengths uncoiling or unfolding as they are drawn from the container 8. FIG. 4 also shows means of providing limited friction as the floss 5 is drawn through slits 9 in the top of the container 8. The slits permit passage of the floss, but the floss rubs the sides of the slits as it is drawn out of the container, resulting in friction between the floss 5 and the container 8. This prevents successive pieces from being drawn out too readily, and encourages the separation of lightly bonded lengths as they are drawn from the container 8. Means for conventionally dispensing pre-cut lengths of the improved dental floss are not limited to those in the described embodiments.

The improved floss may also be provided in a continous roll, much like floss which is currently available. In this embodiment the improved floss is cut by the user so that each piece has a thick portion at each end, and a narrow portion in the center. The floss may be marked or colored to assist the user in locating the centers of thick portions, near which the floss should be cut.

I claim:

1. A new method for using dental floss, said floss comprising a string with a first end portion, a central portion, and a second end portion, the first and second end portions of said string having an increased cross-sectional area relative to the central portion, said end portions also being sufficiently pliable to provide means for wrapping around a finger, said central portion having cross-sectional dimensions suitable for cleaning teeth and gums, said method comprising the steps of wrapping the first end around a finger of one hand wrapping the second end around a finger of the other hand, and using the said central portion to clean the teeth and gums, wherein said ends with increased cross-sectional areas are comfortable and easy to grasp while using said central portion.

2. The dental floss of claim 1, wherein the average cross-sectional area of said end portions is at least 20% greater than the average cross-sectional area of said central portion.

3. A new method for using dental floss, said floss comprising a string with a first end portion, a central portion, and a second end portion, the first and second end portions of said string each having greater width than the central portion, said end portions also being sufficiently pliable to provide means for wrapping around a finger, said central portion having cross-sectional dimensions suitable for cleaning teeth and gums, said method comprising the steps of wrapping the first end around a finger of one hand, wrapping the second end around a finger of the other hand, and using the said central portion to clean the teeth and gums, wherein said ends with increased cross-sectional areas are more comfortable and easy to grasp while said central portion.

4. The dental floss of claim 3, wherein the average width of said end portions is at least 20% greater than the average width of said central portion.

5. An improved dental floss comprising a string with a first end portion, a central portion, and a second end portion, wherein:
    (a) said central portion of said floss has cross-sectional dimensions suitable for use in cleaning teeth and gums, and
    (b) said first and second end portions are coated with a flexible coating selected from the group consisting of a resin, rubber, wax, and elastomer, said end portions being sufficiently pliable to provide means for wrapping around a finger, said coating giving said end portions of floss increased cross sectional dimensions, with respect to said centrl portion, wherein said end portions of floss have improved frictional and tactile properties, relative to said central portion.

* * * * *